United States Patent [19]
Faltys et al.

[11] Patent Number: 6,157,861
[45] Date of Patent: Dec. 5, 2000

[54] SELF-ADJUSTING COCHLEAR IMPLANT SYSTEM AND METHOD FOR FITTING SAME

[75] Inventors: Michael A. Faltys, Northridge, Calif.; Gerald E. Loeb, Kingston, Canada

[73] Assignee: Advanced Bionics Corporation, Sylmar, Calif.

[21] Appl. No.: 09/202,751

[22] PCT Filed: Jun. 19, 1997

[86] PCT No.: PCT/US97/10590

§ 371 Date: Dec. 15, 1998

§ 102(e) Date: Dec. 15, 1998

[87] PCT Pub. No.: WO97/48447

PCT Pub. Date: Dec. 24, 1997

Related U.S. Application Data

[60] Provisional application No. 60/020,206, Jun. 20, 1996.

[51] Int. Cl.$^7$ ........................................... A61N 1/36
[52] U.S. Cl. ................................................ 607/57
[58] Field of Search .................... 607/55, 56, 57

[56] References Cited

U.S. PATENT DOCUMENTS

| | | | |
|---|---|---|---|
| 3,751,605 | 8/1973 | Michelson | 179/107 |
| 4,099,035 | 7/1978 | Yanick | 179/107 |
| 4,267,410 | 5/1981 | Forster et al. | 179/107 |
| 4,284,856 | 8/1981 | Hechmair et al. | 179/107 |
| 4,400,590 | 8/1983 | Michelson | 179/107 |
| 4,408,608 | 10/1983 | Daly et al. | 128/421 |
| 4,428,377 | 1/1984 | Zollner et al. | 128/419 |
| 4,462,411 | 7/1984 | Rickards | 128/746 |
| 4,532,930 | 8/1985 | Crosby et al. | 128/419 |
| 4,577,641 | 3/1986 | Hochmair et al. | 128/746 |
| 4,819,647 | 4/1989 | Byers et al. | 128/642 |
| 5,522,865 | 6/1996 | Schulman et al. | 607/56 |
| 5,626,629 | 5/1997 | Faltys et al. | 607/57 |

FOREIGN PATENT DOCUMENTS

| | | |
|---|---|---|
| 9414376 | 12/1993 | WIPO . |
| 9709863 | 9/1996 | WIPO . |

*Primary Examiner*—Scott M. Getzow
*Attorney, Agent, or Firm*—Bryant R. Gold

[57] ABSTRACT

A self-adjusting implantable cochlear implant system (46) includes an implant portion (50) and an external portion (53). The system provides a device and a way to objectively determine selected psychophysical parameters, such as stimulation threshold, comfort level and loudness resolution, used by the implant portion, which includes an implantable cochlear stimulator (ICS), as it carries out its stimulation function. The input to the system is an electrical stimulation. The outputs of the system include a middle ear reflex (MER) and evoked potentials, such as a compound action potential (CAP) along the auditory/cerebral pathways, both of which are sensed using objective measurement techniques and tools. In accordance with one embodiment, the adjustment process uses the MER for determining a coarse threshold value, and then (using such coarse threshold value as a starting point) uses evoked potentials to determine a more precise o fine threshold value, thereby zeroing in on a desired threshold. Such zeroing-in method is preferably carried out using implanted circuitry (e.g., included as part of the ICS), which implanted circuitry uses an implanted middle ear electrode (54) and a cochlear electrode (56), along with appropriate amplification (58, 64), filtering (60, 66) and processing circuitry (62, 68, 67), to respectively determine the MER response and evoked potentials. Another embodiment uses the presence or absence of the MER to adjust the intensity of electrical stimulation continuously and automatically, thereby relieving the patient from having to perform slow and tedious manual adjustments of the loudness control of a speech processor used with the ICS.

20 Claims, 7 Drawing Sheets

SELF-ADJUSTING COCHLEAR IMPLANT SYSTEM AND METHOD FOR FITTING SAME

This application claims benefit to provisional Application Ser. No. 60/020,206 filed Jun. 20, 1996.

BACKGROUND OF THE INVENTION

The present invention relates to an implantable cochlear stimulator (ICS) and a method for fitting such ICS to a particular patient, where "fitting" refers to the process of determining and setting the amplitude or intensity of the stimuli generated by the ICS to a level or setting that is both effective (allows the ICS to optimally perform its intended function) and comfortable (not excessively loud or painful) for the patient. More particularly, the invention relates to a method of self-fitting an ICS to a particular patient using objective feedback rather than subjective feedback in order to determine stimulation parameters for the patient. The invention further relates to an ICS that includes implantable self-fitting circuitry.

An ICS is an electronic device that helps a profoundly deaf patient to achieve the sensation of hearing by applying electrical stimulation directly to the auditory nerve through the cochlea. An ICS includes electronic circuitry, hermetically sealed for implantation, and an electrode array (comprising a plurality of spaced-apart, independent, individual electrodes) suitable for insertion into the cochlea. An ICS system includes a microphone (for sensing audio sounds), a speech processor (for processing the sensed audio sounds and converting such to electrical stimulation signals), and a cochlear stimulator (for receiving the electrical stimulation signals and directing them to the appropriate electrode or electrodes of the electrode array). Typically, the microphone and speech processor are external components worn or carried by the patient, and the electrical stimulation signals produced by the speech processor are coupled into the implanted cochlear stimulator through an inductive, rf, or other wireless link.

Cochlear stimulators are known in the art, as evidenced, e.g., by U.S. Pat. Nos. 3,751,605 (Michelson); 4,400,590 (Michelson); 4,267,410 (Forster et al.); 4,284,856 (Hochmair et al.); 4,408,608 (Daly et al.); 4,428,377 (Zollner et al.); and 4,532,930 (Crosby et al.). All such stimulators generate electrical stimulation pulses that may be selectively applied to the cochlea of a patient through an appropriate electrode or electrode array.

When the implanted cochlear stimulator (ICS) is initially implanted in the patient, and during follow-up tests and checkups thereafter, it is usually necessary to fit the ICS to the patient. Such "fitting" includes adjustment of the base amplitude or intensity of the various stimuli generated by the ICS from the factory settings (or default values) to values that are most effective and comfortable for the patient. For example, the intensity or amplitude and/or duration of the individual stimulation pulses provided by the ICS must be mapped to an appropriate dynamic audio range so that the appropriate "loudness" of sensed audio signals is perceived. That is, loud sounds should be sensed by the patient at a level that is perceived as loud, but not painfully loud. Soft sounds should similarly be sensed by the patient at a level that is soft, but not so soft that the sounds are not perceived at all.

Fitting and adjusting the intensity of the stimuli and other parameters of a cochlear implant to meet a given patient's needs thus requires determining the electrical stimulation levels at which "sound" is perceived (threshold), at which a comfortable sound level (comfort level) is perceived, and the perceptual loudness growth function resolution within the patient's dynamic range. Heretofore, these psychophysical parameters have been determined by an expert clinician presenting various stimuli to the patient and relying on subjective feedback from the patient as to how such stimuli are perceived. Such subjective feedback typically takes the form of either verbal (adult) or non-verbal (child) feedback. Unfortunately, relying on subjective feedback in this manner is difficult, particularly for those patients who may have never heard sound before and/or who have never heard electrically-generated "sound". For young children, the problem is exacerbated by a short attention span, as well as difficulty in understanding instructions and concepts, such as high and low pitch, softer and louder, same and different. Furthermore, in the developing nervous system of young children, frequent changes in the intensity of the stimuli may be required for optimal benefit. These changes may require frequent refitting sessions or, ideally, continuous adjustment during use in response to the loudness perceived by the brain.

In view of the above, it is evident that a more objective approach is needed for fitting an ICS to a patient. The present invention relates to the use of physiological signals generated by the nervous system to control the level of stimulation that the ICS applies to the cochlea. In order to better understand this concept, it will be helpful to review these phenomena. When neurons are activated by natural or artificial means, they generate pulses of electrical current called action potentials. The current produced by a single neuron is very small, but electrical stimulation, such as is applied by an ICS, tends to recruit large numbers of neurons synchronously. This results in a compound action potential (CAP) that can be recorded electronically in the tissues surrounding the neurons, particularly in the fluid-filled cochlear ducts where the stimulating electrodes of an ICS are usually located. The amplitude of this compound action potential, or CAP, is approximately related to the number of auditory neurons that have been activated by the electrical stimulation. The level of stimulation at which a CAP can first be recorded corresponds approximately to the threshold for hearing (T), or a small, fixed value above that level.

The action potentials produced by auditory neurons are conducted to various relay nuclei of the brainstem, which transform the information into action potentials that are transmitted by other neurons to yet further nuclei and eventually to the perceptual centers in the cerebral cortex. The compound action potentials resulting from patterns of neural activity in these subsequent nuclei can also be recorded electronically, but they are very much weaker, less accessible and more variable. Typically, these are recorded by widely spaced external electrodes on the scalp and enhanced by stimulus-triggered averaging, in which the small and noisy signals recorded following each of thousands of identical stimuli are added together in order to reduce the effects of noise inherent in the electrodes and amplifiers used to detect the scalp potentials. The amplitude of these electrical auditory brainstem responses (EABRs) depends not only on the number of auditory neurons that are initially stimulated, but also on the size and condition of the nuclei, the connections between them, and on descending signals from the perceptual centers that can influence the transformations produced in the relay nuclei. Obtaining and using EABRs to fit an ICS system is tedious and controversial, particularly in children with uncertain developmental status of the brainstem nuclei.

When the nerve signals finally arrive in the perceptual centers, they give rise to the conscious perception of sound and its apparent loudness. When sounds are perceived as being undesirably loud, the brain can employ various mechanisms to reduce the intensity to more desirable levels. In normal hearing, the perceived loudness of sound depends on the amount of acoustic energy that is transmitted through the middle ear to the cochlea. The brain can control this via the mechanical tension produced by two muscles in the middle ear: (1) the stapedius, and (2) the tensor tympani. The brain sends neural signals to these muscle fibers, causing them to produce active mechanical tension which damps the mechanical linkage and reduces the transmission of sound energy. Even when the sensations of sound are produced electronically by an ICS, these middle-ear reflexes (MER) are usually present even though they have no effect on the electrical stimulation that is actually stimulating the auditory neurons. The level of stimulation at which the middle ear reflex, or MER, appears is associated approximately with the most comfortable loudness (MCL) level of sound perception. This reflex, in turn, may be measured by any of three different methods or means.

First, the contraction of the muscle has been observed visually when cochlear stimulation is applied during the surgical implantation of the ICS. This is problematic, however, because it depends on the level and nature of the anesthesia.

Second, the contraction of the muscle has been inferred from measurements of the acoustic impedance during cochlear stimulation. This requires attaching a tube to the external ear canal to apply air pressure and measure small changes in the response to pressure impulses. Children must usually be sedated, which may interfere with the reflex, and the recorded response depends on the mechanical details of the middle ear linkage, which may be poorly developed or damaged as a result of the deafness.

Third, the electrical activity that accompanies the muscle contractions can be recorded as the electromyogram (EMG).

The first two methods described above have been employed in the fitting of ICS systems, but they are not suitable for frequent recalibration. The last method has been employed by researchers studying the nervous system, but not as a clinical technique because of the relative inaccessibility of the middle ear muscles.

SUMMARY OF THE INVENTION

The present invention teaches methods and techniques whereby recording electrodes may be chronically implanted in or near one or both of the middle ear muscles during the implantation of the ICS. The EMG is recorded as a broadband, amplitude-modulated AC signal whose general amplitude or envelope corresponds to the strength of the command signals from the brain. By comparing the amplitude of this envelope with and without stimulation, the strength of the middle ear reflex, or MER, may be measured frequently and accurately regardless of the condition of the middle ear mechanical linkage. By employing chronically implanted recording electrodes and telemetry, as taught in this invention, these measurements may be obtained from the fully alert patient in order to determine a level of stimulation that corresponds approximately to the most comfortable loudness, or MCL.

An advantage offered by recording the middle ear reflex by EMG and telemetry from the ICS is that it may be used continuously to adjust the loudness of the stimulation during actual use. Further, ICS system frequently employ automatic gain control (AGC) circuitry to compress the wide dynamic range of acoustic signals into the highly limited dynamic range of electrical stimulation between T and MCL. It is difficult to do this electronically in a manner that agrees with the loudness perceived by the patient because this perceived loudness depends complexly on the spectrum and context of the sound and the mental state of the patient. In contrast, the middle ear reflex, or MER, reflects the actual perception of the patient, occurring only when the brain desires the loudness of the sound to be reduced. By using the presence or absence of this reflex to adjust the intensity of electrical stimulation continuously and automatically, as taught by the present invention, the patient is thus relieved of the slow and tedious process of making frequent manual adjustments of the loudness control on the speech processor.

In one embodiment, the present invention thus provides a self-adjusting ICS and a method for self-adjusting an ICS. The method uses an ICS in a closed-loop system that "zeros-in" on the relevant psychophysical parameters, such as stimulation threshold, comfort level and loudness growth function resolution within the patient's dynamic range.

The self-adjusting ICS utilizes a specialized electrode implanted and placed near the stapedius or tensor tympani muscle in order to sense the middle ear reflex response. The use of such specialized electrode advantageously eliminates the need to use external equipment, such as an impedance bridge (which impedance bridge would otherwise have to be used to detect the stapedius reflex response), and thus increase reliability and sensitivity. Implanted circuitry is also used within the self-adjusting ICS to internally sense an evoked potential using a stimulation electrode, rather than sensing such evoked potential through an external ear clip or other surface electrode. Using an internal electrode in this manner advantageously provides a much stronger and less noisy signal than could be obtained using a surface electrode. Further, using internally-measured evoked potentials allows the actual stimulus waveform to be used to cancel the stimulus-created artifact through the use of a blanking amplifier.

The invention may thus be broadly characterized as a self-adjusting or self-fitting ICS that includes cochlea stimulus means for selectively generating a stimulus of a specified intensity on any one of a plurality of channels, middle ear reflex sensing means for sensing a middle ear reflex in response to a stimulus applied by the stimulus means; evoked potential sensing means for sensing an evoked potential in response to a stimulus generated by the stimulus means; and microcontroller means for controlling the cochlea stimulus means, evoked potential sensing means and middle ear reflex sensing means to determine the stimulation threshold, most comfortable loudness, and/or other psychophysical parameters of the ICS.

The invention may further be characterized, in accordance with one aspect thereof, as an implantable cochlear stimulator which includes means for electrically stimulating the cochlea, and means for recording electromyographic potentials from one or more muscles of the middle ear.

Additionally, the invention may be broadly characterized as an automated method of determining a suitable range of stimulus intensity for an implantable cochlear stimulator (ICS). Such method includes the steps of: (1) delivering a test stimulation level to one or more of the intracochlear electrodes of the ICS; (2) measuring a physiological response from the subject; (3) adjusting the stimulation level up or down according to a preprogrammed algorithm, and repeating the measurement until a desired response occurs;

and (4) automatically recording the final stimulation level determined by the algorithm and using this value, or a value derived by a predetermined function of the recorded value, to determine the intensity of stimulation to be delivered during the normal operation of the ICS.

It is thus a feature of the invention to provide a self-adjusting or self-fitting ICS that is readily fitted to a particular patient without the necessity of relying on subjective feedback from the patient.

It is another feature of the invention to provide a closed-loop fitting procedure that zeros-in on the needed electrical dynamic range using the EMG recorded from at least one middle ear muscle, and the compound action potential (CAP) recorded from the cochlea.

It is a further feature of the invention to provide a method of continuously adjusting the stimulation levels generated by the ICS that avoids the necessity of receiving subjective feedback or manual intervention by the patient during normal use of the ICS system.

It is an additional feature of the invention, in one embodiment thereof, to provide a self-adjusting or self-fitting ICS that does not rely on the integrity of the middle ear, and which avoids the use of surface electrodes when measuring evoked potentials.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

Figure 1:
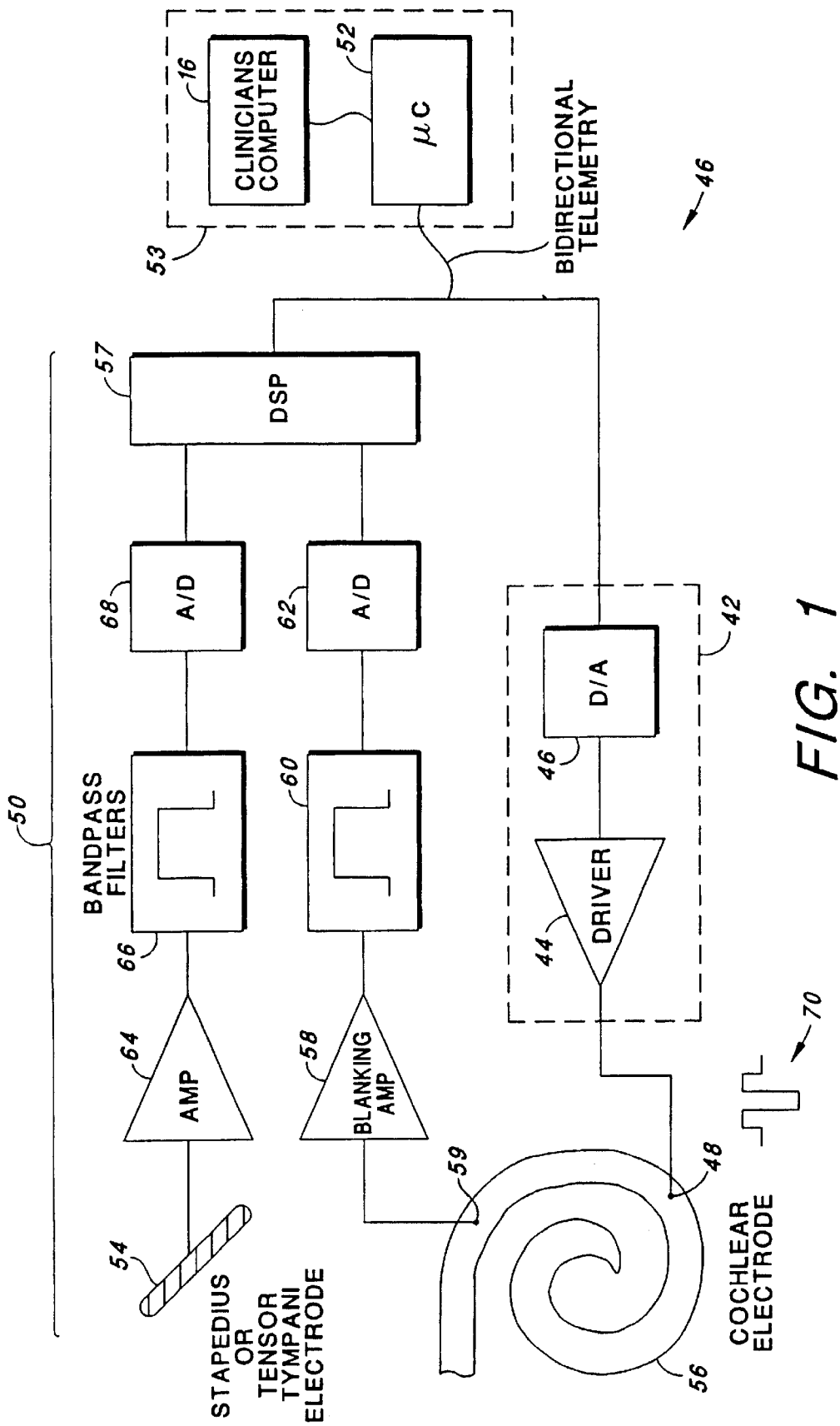
FIG. 1 is a block diagram of an implantable self-adjustable cochlear prosthesis made in accordance with the invention.

The following description is of the best mode presently contemplated for carrying out the invention. This description is not to be taken in a limiting sense, but is made merely for the purpose of describing the general principles of the invention. The scope of the invention should be determined with reference to the claims.

A representative ICS that may be used with the present invention is disclosed in U.S. Pat. No. 5,522,865, incorporated herein by reference. A representative fitting system, or fitting tool, that may be used in lieu of, or as a supplement to, the present invention is disclosed in U.S. patent application Ser. No. 08/456,141, filed May 31, 1995, also incorporated herein by reference. A representative electrode array that may be used with the ICS is shown in U.S. Pat. No. 4,819,647, which patent is likewise incorporated herein by reference.

Before describing the invention, the following glossary of terms is provided.

Bi-Phasic Pulse: A balanced stimulation pulse delivered in the cochlea from the implant. Balanced indicates that an equal amount of charge is delivered positively as is delivered negatively in order to eliminate any DC component.

Blanking Amplifier: An amplifier that gates off coincident with the delivery of an electrical stimulation pulse generated by the cochlear prosthesis so that stimulus-induced artifacts may be canceled out, allowing lower level signals to not be lost.

Channel: A selected pair of electrodes capable of applying a given stimulus to a desired location within the cochlea. See "ICS."

Clinician's Computer: A computer used by the clinician or audiologist that presents a display of the fitting process and allows parameters to modified to optimize fitting.

Closed-Loop System: A system that uses feedback to "zero-in" on a specified output.

Comfort Level: An electrical stimulation level on a single channel that is perceived as comfortably loud to the patient.

Compound Action Potential (CAP): An electrical potential recordable in tissues surrounding neurons resulting from recruitment of large numbers of neurons acting synchronously in response to electrical stimulation applied by a cochlear stimulator.

Dynamic Range: Electrical dynamic range is the range between Electrical Threshold and Comfort Level. Sound intensity dynamic range is the range in which input sound intensities are mapped into the electrical dynamic range.

Evoked Potential: Measured localized central nervous system potentials correlated with an external sensory event. Evoked potential signals tend to be very noisy due to surface (non-direct) electrode placement and other bodily electrical activities. As a result, evoked potentials are best identified by correlation with an external trigger.

Electrical Threshold: For purposes of this application, the minimum electrical stimulation level that can be perceived by the patient in a given channel of the ICS.

Electromyogram (EMG): The electrical activity that accompanies the muscle contractions. EMG is generally recorded as a broadband, amplitude-modulated AC signal whose general amplitude or envelope corresponds to the strength of the command (neural) signals from the brain.

Fitting: The process of customizing a Cochlear Prosthesis to a patient by setting the appropriate psychophysical parameters.

ICS: An Implantable Cochlear Stimulator, including an electrode array having spaced-apart electrodes adapted for insertion into the cochlea. The ICS typically includes multiple channels, each of which may provide stimuli to a selected pair of the spaced-apart electrodes (bipolar stimulation), and/or to a selected one of the spaced-apart electrodes and a reference electrode (monopolar stimulation). Each channel thus effectively delivers a stimulus to a different section or location of the cochlea.

Impedance Bridge: A standard audiometric instrument which, for this application, measures middle ear compliance for different pressures and measures the stimulation evoked stapedius reflex.

Ipsilateral: On the same side of the head, in this case on the same side as the implant.

Microcontroller ("µC"): A small computer designed for real-time (fast-response) applications.

Middle Ear Compliance: A measure of the ability of the middle ear to transmit energy.

Mismatched Negativity: An evoked potential that is created by introducing an "odd-ball" or "deviant" stimulus into a regular stimulus pattern.

Middle Ear Reflex (MER): Mechanical tension produced by the stapedius and tensor tympani, two muscles of the middle ear, in response to neural signals received from the brain. MER may be measured by comparing the amplitude of the MEG envelope with and without stimulation.

Most Comfortable Level (MCL): The level of stimulation at which a middle ear reflex first appears.

Myogenic Noise: Muscle noise, usually electrical noise. For purposes of the present invention, the patient is sedated in order to reduce muscle noise when evoked potentials are being recorded.

Speech Processor (SP): A device used with an ICS that senses audio sounds, converts such sounds to electrical signals, and processes the electrical signals in accordance with a prescribed speech processing strategy to produce stimulation control signals. The stimulation control signals, in turn, are used by the ICS to stimulate the cochlea.

Somatic Events: Muscular contractions caused by accidental electrical stimulation of the facial nerve.

Stapedius Reflex Response: Contraction of the stapedius muscle. Such response occurs when the patient is exposed to an electrical stimulation level of between about 70–100 dB equivalent sensation level. For purposes of the present invention, this response is used to estimate comfortably loud levels for the patient.

Threshold of Hearing (T): The level of stimulation which can be perceived or heard, corresponding generally to the level of stimulation at which a CAP can first be recorded, or a small fixed value above that level.

Tri-Phasic Pulse: A balanced stimulation pulse delivered in the cochlea from the implant. See "Bi-phasic". A tri-phasic pulse better models spiral ganglion firing, assisting in the recovery of neurons and possibly reducing unwanted stimulation artifacts.

Referring first to FIG. 1, there is shown a simplified functional block diagram of a preferred implanted self-fitting or self-adjusting cochlear implant system 46 made in accordance with the present invention. It is to be emphasized that which is shown in FIG. 1 is greatly simplified in order to depict the basic functions that are carried out by the implanted and external portions of the system 46 as the present invention is carried out. As seen in FIG. 1, the system 46 includes an implanted portion 50 (referred to hereafter as the implant 50) and an external (or non-implanted) portion 53. The external portion, in turn, is usually made up of a microcontroller (µC) 52 coupled to a clinician's computer 16. The µC 52 may be realized using a conventional speech processor (SP) with a special interface which allows it to be connected directly to the clinician's computer 16, as is known in the art. A much more detailed description of a preferred cochlear implant 50 may be found, e.g., in the previously referenced U.S. Pat. No. 5,522,865.

As indicated, the implant 50 includes, or is coupled to, a suitable microcontroller (µC) 52. It is noted that for some embodiments of the implant 50, the µC 52 may comprise part of an external speech processor. For other embodiments of the invention, however, the µC 52 may comprise part of an internal or implanted speech processor. Regardless of its location, it is the µC 52 that provides the necessary control signals to control the operation of the implant 50. Hence, the µC 52 comprises a main component of the stimulation system.

In a conventional cochlear implant, the control signals from the µC 52 (which are digital signals) are converted to analog signals by a suitable digital-to-analog (D/A) converter 46'. The resulting analog signals output from the D/A converter 46' are then applied to a suitable driver circuit 44 for application to a cochlear electrode array 56. Of course, much additional circuitry is used to carry out these basic functions, such as modulating the control signals to inductively couple them through the skin of the patient to an implanted unit (when required), demodulating the received signals, decoding the control signals to extrapolate the control information contained therein, generating the appropriate stimulus signals, and applying such stimulus signals to the designated electrode pair or channel of the electrode array. However, for purposes of the present invention, it is sufficient to consider the conventional cochlear implant circuitry as that which performs the two basic functions shown within the dotted line 42 of FIG. 1, coupled to a suitable µC 52 and electrode array 56. As indicated above, these two basic functions are represented by the D/A converter 46, which converts the stimulation control signals obtained from the µC 52 to analog signals, and then applies such converted signals to a selected electrode 48 of the cochlear electrode array 56 through the electrode driver 44.

In addition to the basic cochlear implant functions described above, the self-adjusting cochlear implant 50 of the present invention includes at least one additional electrode not typically found within a cochlear implant unit. That is, a specialized electrode 54 is placed near the stapedius or tensor tympani muscle. Second, a separate electrode 59, which may comprise one of the electrodes of the electrode array 56, is placed in or near the cochlea. The separate electrode 59 may comprise part of the electrode array 56, or may be separate from the array 56.

The stapedius/tensor tympani electrode 54 is connected to a suitable amplifier 64, the output of which is filtered by a bandpass filter 66. The output of the filter 66 is then converted to an appropriate digital signal by analog-to-digital circuit 68, which digital signal is then directed to a digital signal processor (DSP) 57, and then coupled to the µC 52.

In operation, the stapedius/tensor tympani electrode 54, which may include any suitable transducer that converts mechanical motion to an electrical signal, such as a small piezoelectric element, senses movement of the stapedius muscle and generates an electrical signal as a function of such sensed movement. Alternatively, the electrode 54 may be positioned to best sense the EMG. The signal sensed by electrode 54, which represents a measured response of the stapedius muscle or the MER, is then amplified, filtered and digitized by the amplifier 64, filter 66, A/D converter 68, and DSP 57, and presented to the µC 52 as a digital signal through bidirectional telemetry.

Still referring to FIG. 1, the evoked potential electrode 59 is similarly connected to an amplifier 58, an adjustable bandpass filter 60, an analog-to-digital converter 62, and the DSP 57. Evoked potentials sensed through the electrode 59 are thus amplified by the amplifier 58, filtered by the filter 60, digitized by the A/D converter 62, processed by the DSP 57, and presented to the μC 52 as a digital signal. Advantageously, the amplifier 58 comprises a blanking amplifier. Such blanking amplifier may, for example, be blanked off at all times except during a narrow window of time during which the evoked response, e.g., the CAP, if present, will appear, thereby blocking myogenic and other noise from being processed by the evoked response circuitry at times other than the narrow window detection time. More importantly, the blanking amplifier 58 may be blanked coincident with the application of a stimulus signal to the cochlear electrode array, thereby preventing any stimulus-created artifacts from being sensed through the amplifier 58. Such blanking action thus makes it easier to sense the evoked potentials because such evoked potentials might otherwise be masked out by the usually much larger stimulus-induced artifacts.

Further illustrated in FIG. 1 is a graphical depiction of a tri-phasic pulse 70. It is important that the electrical stimulus which is applied to the electrodes of the electrode array 56 be charged-balanced, meaning that such stimulus should have positive components that are equal to its negative components. The tri-phasic pulse 70 achieves this goal by having the sum of its respective leading and trailing small positive portions be substantially equal to one larger negative middle portion.

Figure 2:
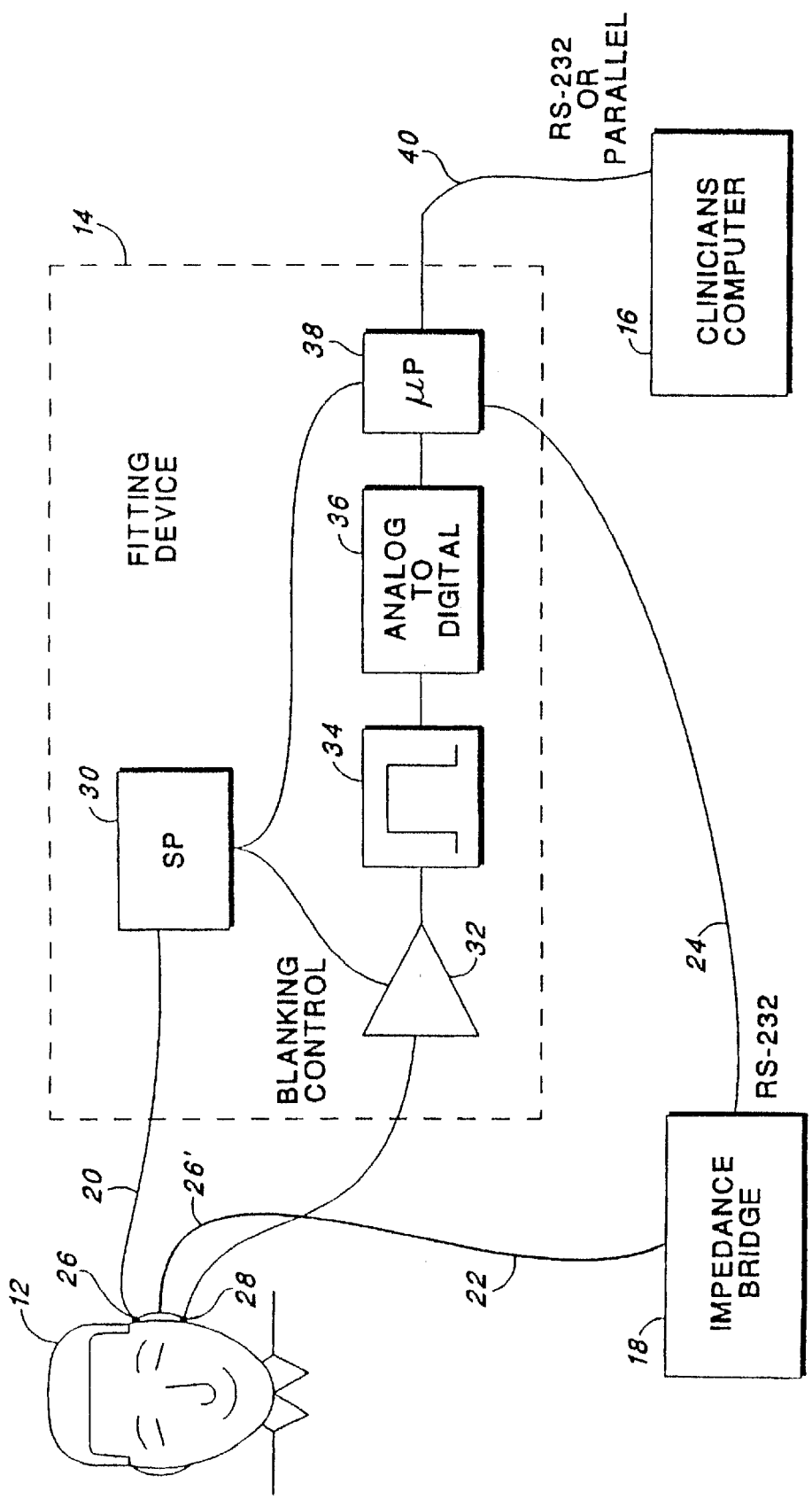
FIG. 2 is a block diagram of an external self-fitting cochlear prosthesis system.

In contrast to the implantable self-adjusting cochlear prosthesis system shown in FIG. 1, a block diagram of an external self-fitting cochlear prosthesis system is shown in FIG. 2. As needed or desired, the external system may be used to supplement or complement that which is achieved using the implant system 46 shown in FIG. 1.

In FIG. 2, as with FIG. 1, it is assumed that a patient 12 has an ICS implanted in or near at least one of his or her ears. A fitting device 14 sends stimulation control signals, or "input" signals, to the ICS through a first wire 20. Typically, the wire 20 is connected to a headpiece 26 which is magnetically held over the ICS, and which headpiece inductively couples the stimulation control signals into the ICS, as is known in the art.

To this end, the fitting device 14 includes a speech processor (SP) 30 coupled to a microcontroller (μC) or microprocessor (μP) 38. The μC 38 controls the SP 30 so that the appropriate stimulation control signals are generated. The fitting device 14 further includes an evoked potential blanking amplifier 32 connected to a bandpass filter (BPF) 34. The BPF 34, in turn, is connected to an analog-to-digital (A/D) converter 36, the output of which is connected to the μC 38. The input of the blanking amplifier 32 is connected by way of wire 26 to an earlobe electrode 28. Evoked potentials sensed through the earlobe electrode 28 are thus amplified by the amplifier 32, filtered by the BPF 34, converted to a digital value by the A/D converter 36, and presented to the μC 38 as a digital value.

Still with reference to FIG. 2, a conventional impedance bridge 18 is coupled to the middle ear of the patient 12 by way of cable 22, which cable 22 includes sufficient conductors to enable the impedance bridge 18 to measure the compliance of the patient's middle ear. Such compliance may be measured in conventional manner. The impedance bridge 18 typically employs a standard RS-232 serial interface, or equivalent data interface, through which data may be sent to the fitting device 14, thus allowing compliance data measured within the patient's middle ear to be provided to the μC 38 through the connecting cable 24.

A clinician's computer 16 may also be coupled to the μC 38 of the fitting device 14 by way of cable 40, connected to either a serial or parallel port. Use of the computer 16 allows the user of the computer, i.e., the clinician and/or audiologist, to track and control the activities being carried out by the fitting device 14. The computer 16 is especially helpful in that it typically includes a suitable display screen, or other output device, on which graphs, tables, reports and other useful information associated with the fitting process may be displayed and/or printed.

The self-fitting cochlear prosthesis system shown in FIG. 2 determines the thresholds of the patient 12 for each channel of his or her ICS by providing a known input signal to the ICS from the SP 30 over the signal line 20 and measuring the resulting output stapedius reflex response (using the impedance bridge 18) and/or the measured output evoked potentials (using the blanking amplifier 32, filter 34, and A/D converter 36). More particularly, as described more fully below in conjunction with the flow chart shown in FIGS. 3A, 3B, and 3C, the self-fitting system of the invention zeros-in on the needed threshold information by first using the stapedius reflex response to determine a coarse threshold level, which stapedius reflex response can be obtained relatively quickly; and then uses such coarse threshold level as the starting point for a more precise hunt for a fine threshold level using the measured evoked response.

Figure 3A:
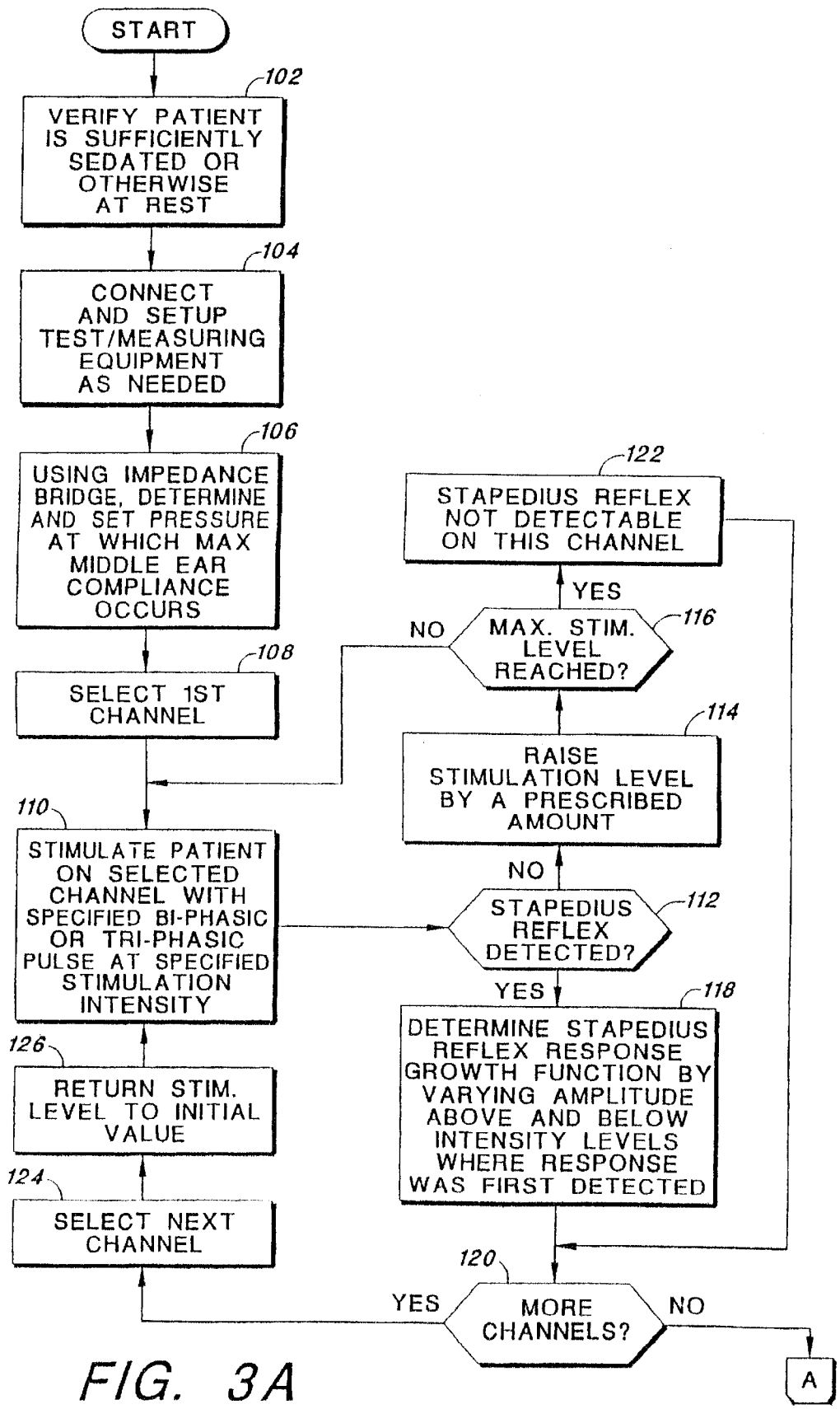
FIGS. 3A, 3B and 3C respectively show various portions of a flow chart that shows one method of fitting an ICS in accordance with the invention.
Figure 3B:
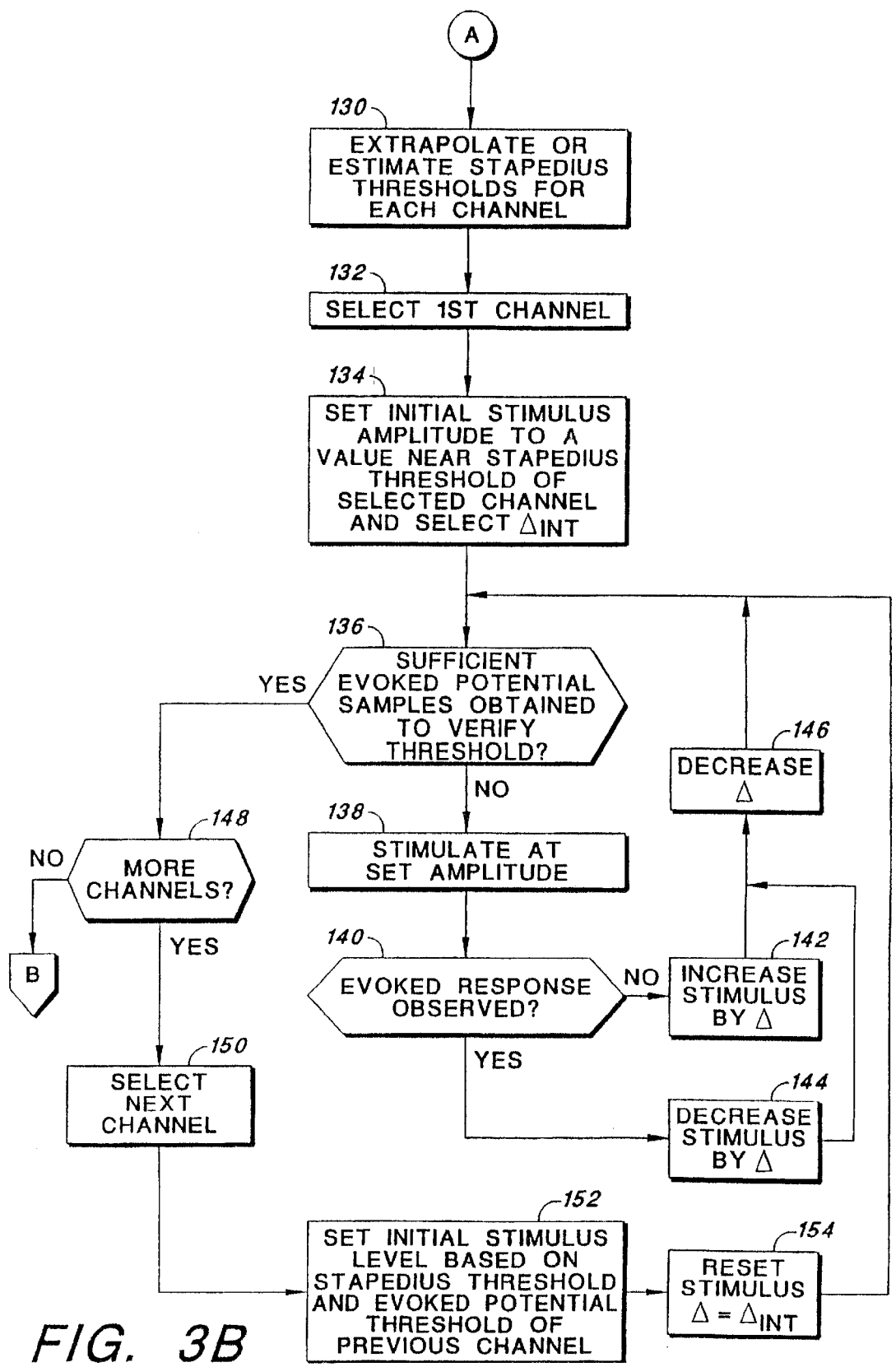
Figure 3C:
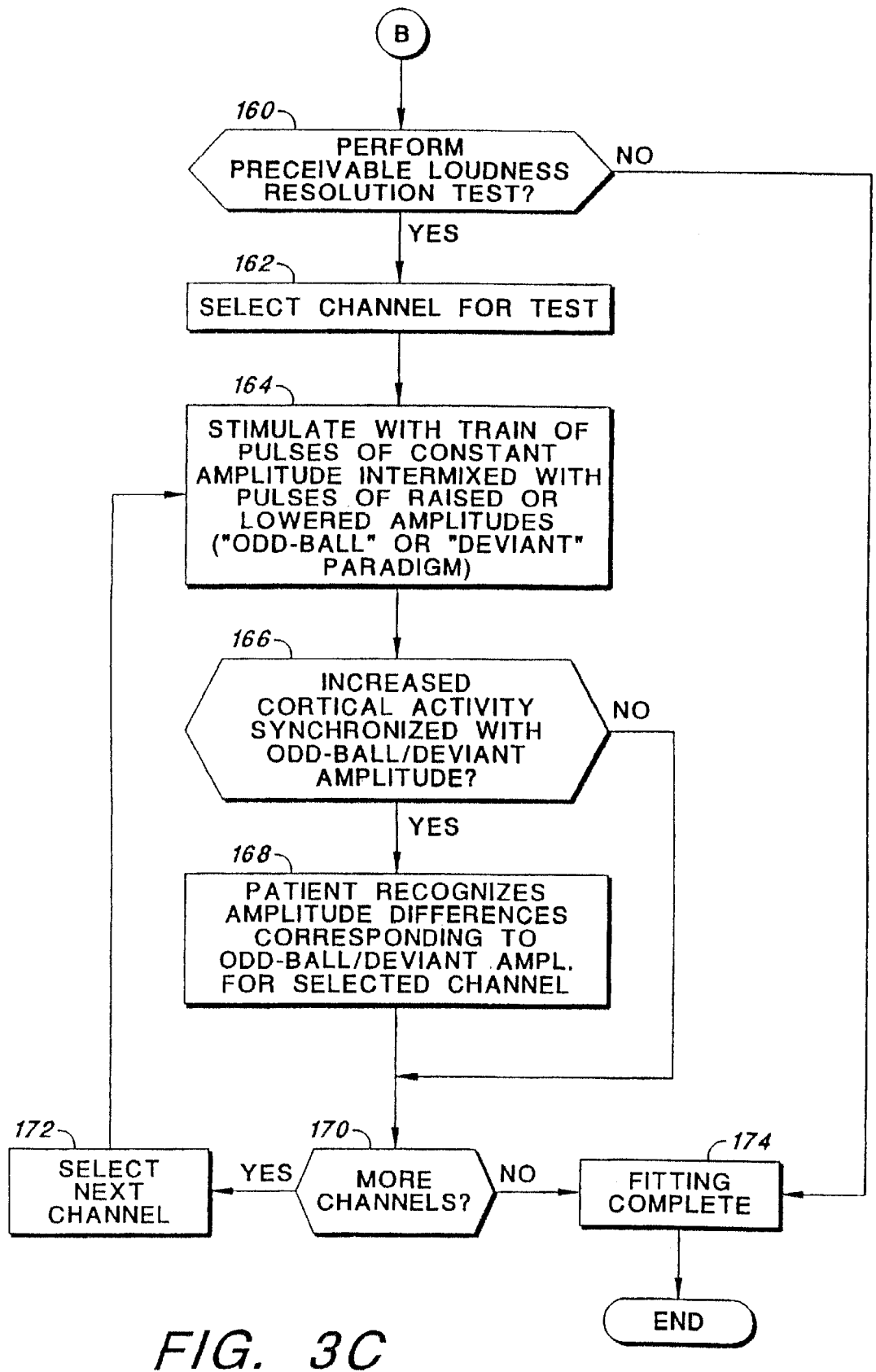

Turning next to FIGS. 3A, 3B and 3C, a flow chart is shown that illustrates the self-fitting method used by the present invention to determine the patient thresholds for each channel of an ICS. Each main step of the self-fitting method or process is depicted as a "block" or "box", each of which has a reference numeral assigned thereto to aid in the description that follows. While various portions of the method are depicted in each of FIGS. 3A, 3B or 3C, it comprises a single flow chart, and reference may hereafter be made collectively to FIGS. 3A, 3B and 3C as simply "FIG. 3".

The method shown in FIGS. 3A–3C is directed to the method used with the external self-fitting cochlear prosthesis system shown in FIG. 2. However, the same basic method is followed when using the implanted system of FIG. 1, with the exceptions indicated.

Turning first then to FIG. 3A, it is seen that a first step of the method involves verifying the patient is sufficiently sedated, or otherwise at rest (block 102). Such step assures that the method may be carried out without interfering myogenic or other noise. Once the patient is sufficiently sedated, then the necessary equipment, e.g., the impedance bridge 18 and the fitting device 14, as shown in FIG. 2, is set-up and connected to the patient (block 104).

With the equipment connected as illustrated in FIG. 1, the impedance bridge is calibrated by determining and setting that pressure value (loudness) at which maximum middle ear compliance occurs (block 106). Such pressure value may thereafter serve as a "threshold" value for detecting when a given sound "input" to the patient's ear causes a stapedius reflex to occur on a given channel.

The process of detecting the stapedius reflex on each channel includes selecting a first channel (block 108), and the then stimulating the patient on the selected channel with a specified bi-phasic or tri-phasic pulse at a specified stimulation level (block 110). For example, the specified bi-phasic or tri-phasic pulse may have a width of from 75 to 150 μsec, and the specified stimulation level may initially range from 6 dBu to 30 dBu. A determination is then made as to whether the applied stimulus caused a stapedius reflex (block 112). If not (NO branch of block 112), then the stimulation level is raised by a prescribed amount, e.g., 6 dBu (block 114), and a check is made as to whether the raised stimulation level exceeds a maximum stimulation level (block 116). The maximum stimulation level is typically 60 dBu or other specified FDA charge limits. If the maximum limit has not been reached (NO branch of block 116), then a tri-phasic or bi-phasic pulse of the raised stimulation level is applied to the patient and the process repeats (blocks 110, 112, 114). If the maximum limit has been reached (YES branch of block 116), then that means a stapedius reflex is not detectable on the specified channel (block 122).

When a stapedius reflex is detected (YES branch of clock 112) in response to the applied stimulus of the specified intensity level, then the stapedius reflex growth function is determined by varying the amplitude above and below the intensity level at which the stapedius reflex response was first detected. Knowing the growth function allows one to predict how the stapedius reflex grows (changes) when subjected to stimuli near the threshold, and helps determine the threshold through extrapolation.

Once the stapedius reflex of the first channel has been determined (or a determination has been made that the stapedius reflex is not detectable on the first channel), then a determination is made as to whether there are any more channels for which the stapedius reflex measurement needs to be determined (block 120). If so (YES branch of block 120), then the next channel is selected (block 124), and the stimulation intensity level is returned to its specified initial value. Then the process repeats for the newly selected channel (blocks 110 through 118).

If all of the channels have been stimulated in an effort to determine the point at which a stapedius reflex occurs (NO branch of block 120), then the stapedius threshold is extrapolated or estimated for each channel (block 130, FIG. 3B). If stapedius data was obtained (as determined, e.g., at blocks 110, 112, 118), then such data is used to extrapolate the threshold. If no stapedius data was detectable for a given channel (see, e.g., block 122), then the threshold is estimated to be 6 dBu.

Advantageously, the stapedius thresholds determined as described above, by extrapolation and/or estimation, represent a coarse, or rough, determination of the desired stimulation thresholds to be used by the ICS. In order to further "zero-in" on the such threshold, the present invention uses an evoked response measurement. More particularly, as shown in FIG. 3B, a first channel is selected (block 132). An initial stimulus amplitude is then set at a value near the previously-determined stapedius threshold for the selected channel, and an appropriate adjustment interval, $\Delta_{INT}$, is specified (block 134).

One of the drawbacks of using evoked potentials for determining the appropriate stimulation threshold is that a rather large sample of evoked potentials must be obtained in order to assure a statistically valid measurement. For example, evoked potentials may require from 32 to 1000 samples using the external system of FIG. 1. One of the advantages of the implanted system of FIG. 2 over the external system of FIG. 1 is that the number of samples required for the implanted system is usually reduced by a factor of at least 2.

In view of the above, a first determination at the beginning of the loop in which the evoked potential measurements are made is to determine whether sufficient evoked potential samples have been obtained to produce a statistically valid indication of threshold (block 136). If not (NO branch of block 136), which will always be the case when the evoked potential test is first started, then a stimulus is applied that has a specified starting intensity (block 138), i.e., an intensity near that of the stapedius reflex determination. A determination is then made as to whether such applied stimulus evoked a response (block 140). If not (NO branch of block 140), then the stimulus intensity is increased by the specified adjustment interval $\Delta$ (block 142). If so (YES branch of block 140), then the stimulus intensity is decreased by the specified adjustment interval $\Delta$ (block 144). The size of the adjustment interval $\Delta$ (for use during the next pass through the loop) is then decreased (block 146).

The adjusted stimulus (which is either increased or decreased over the prior stimulus, depending upon whether an evoked response was observed or not) is then used for a next pass through the evoked potential loop (blocks 136 through 146). This process continues, with repeated passes through the evoked potential loop continuing until a sufficient number of evoked potentials have been obtained (YES branch of block 136), with each pass using a decreased or smaller $\Delta$, in order to zero-in on the evoked potential threshold.

After sufficient samples of evoked potential have been obtained for the first channel, the process repeats for the other channels. That is, once the evoked potential data has been obtained for one channel (YES branch of block 136), a determination is made as to whether there are any more channels (block 148). If so (YES branch of block 148), then the next channel is selected (block 150), and the initial stimulus intensity is set to an initial value for that channel based on the stapedius threshold of that channel and based on the evoked potential threshold of one or more previous channels (block 152). Further, the value of the adjustment interval $\Delta$ is reset to $\Delta_{INT}$ (block 154), and the evoked potential for the newly-selected channel is determined as previously described (blocks 136 through 154).

Once all of the channels have been subjected to the evoked-potential-determining loop (NO branch of block 148), then a determination is made as to whether a perceivable loudness resolution test is to be performed (block 160, FIG. 3C). The performance of such a test is preferably an option that may be selected by the clinician. If such a test is not to be performed (NO branch of block 160), then the self-fitting method is completed (block 174). If such a test is to be performed (YES branch of block 162), then the channel on which the test is to be performed is selected (block 162). The selected channel is then stimulated with a train of pulses of constant amplitude intermixed with pulses of raised or lowered amplitudes (a stimulation pattern known as an "odd-ball" or "deviant" paradigm). Based on the applied stimulation from such odd-ball or deviant paradigm pulse train, a determination is made as to whether there is any increased cortical activity that is synchronized with the odd-ball/deviant amplitude (block 166). If so (YES branch of block 168), then that indicates that the patient recognizes amplitude differences corresponding to the odd-ball/deviant amplitude channel (block 168). If there is no increased cortical activity synchronized with the odd-ball/deviant amplitude (NO branch of block 166), then that indicates the contrary result, i.e., the patient does not recognize amplitude differences corresponding to the odd-ball/deviant amplitude.

Once a first channel has been subjected to the perceivable loudness resolution test as described above, then a determination is made as to whether additional channels remain which need to be subjected to the same test. If so (YES branch of block 170), then a next channel is selected (block 172), and the perceivable loudness resolution test is repeated for the selected channel (blocks 164 through 168). If not (NO branch of block 170), then the fitting is completed (block 174).

When the implanted fitting system is used (FIG. 1) instead of the external system (FIG. 2), then essentially the same method described in FIGS. 3A–3C is used to zero-in on the appropriate threshold settings, with some modification. In particular, the principal modification required by the implanted system—and, indeed, an advantage of the implanted system—is to remove the step of using the impedance bridge to determine the stapedius reflex threshold. Rather, the stapedius reflex electrode 54 (FIG. 1) provides a quantitative measure of the stapedius reflex response, which measure may be logged and/or analyzed by the μC 52 in order to determine whether a particular stapedius reflex response is to be deemed a stapedius reflex detection (block 112, FIG. 3A).

It is thus seen that by using the external fitting system shown in FIG. 2, or the internal system shown in FIG. 1, and through the use of a fitting method substantially as shown in FIGS. 3A through 3C, that the present invention provides a self-fitting ICS that is readily fitted to a particular patient without the necessity of relying on subjective feedback from the patient as the fitting process is carried out. It is further seen that the invention provides a closed-loop fitting procedure that advantageously zeros-in on the needed threshold value(s) by using a stapedius reflex response to determine a coarse threshold value(s), and evoked potentials to refine the coarse threshold value(s) to a fine threshold value(s).

Moreover, when the implanted fitting system is employed (FIG. 1), it is seen that the invention provides a self-fitting ICS that does not rely on the integrity of the middle ear, and which avoids the use of surface electrodes when measuring evoked potentials.

Figure 4:
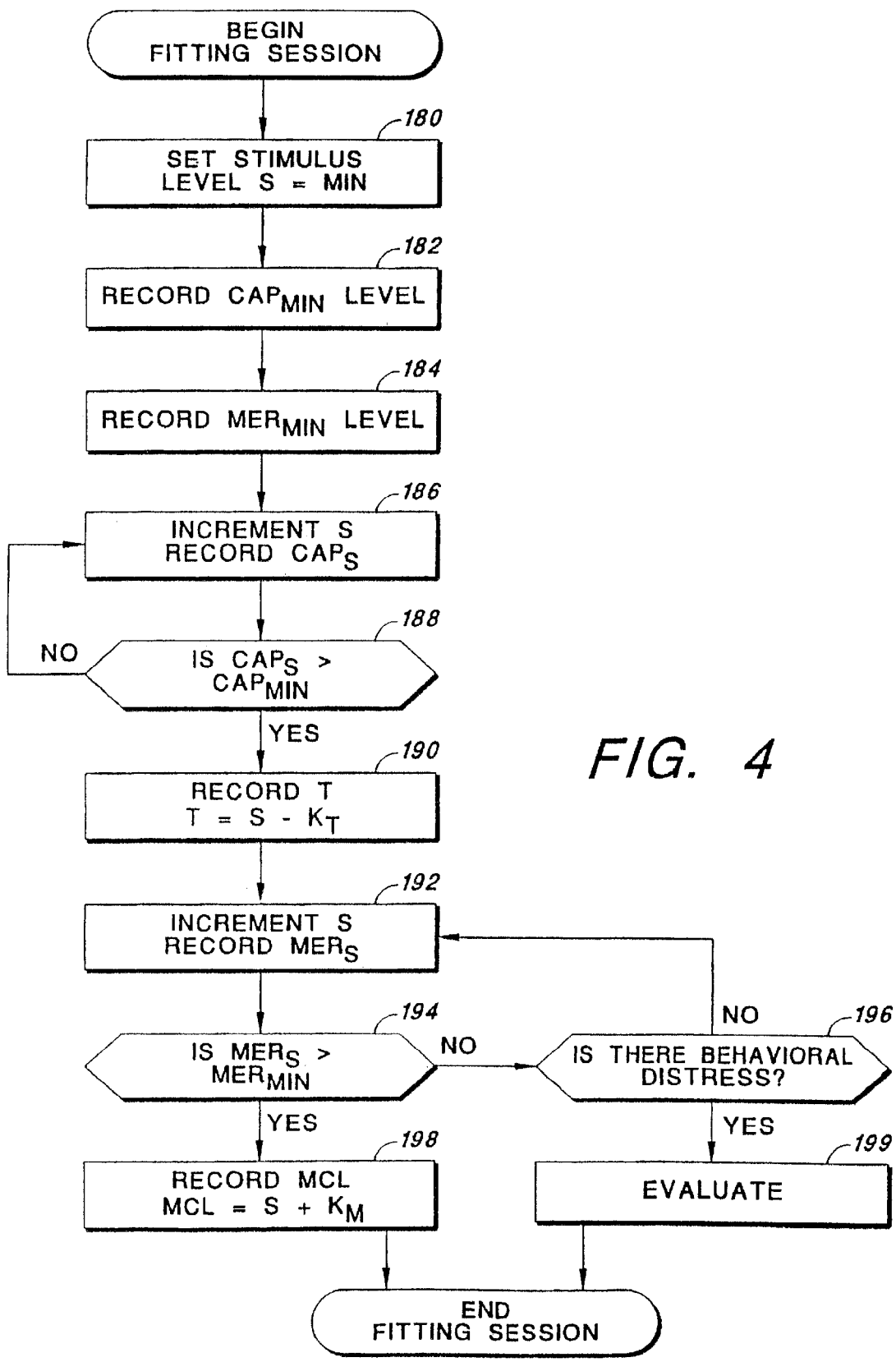
FIG. 4 is a flow chart that depicts another method of a fitting session to determine the threshold of hearing (T) and the most comfortable level (MCL) settings for an ICS.

Turning next to FIG. 4, a flow chart is shown that depicts a preferred fitting session that may be used to determine the threshold of hearing (T) and the most comfortable level (MCL) settings for an ICS using the implanted system (FIG. 1). As seen in FIG. 4, once the fitting session begins (i.e., once the configuration shown in FIG. 1 has been set up), the stimulus level S is set to a minimum value (block 180). Then, a corresponding $CAP_{MIN}$ level is recorded (block 182), as is a corresponding $MER_{MIN}$ level (block 184). Once the $CAP_{MIN}$ and $MER_{MIN}$ levels have been recorded, then the stimulus level is incremented by a prescribed amount, and a corresponding $CAP_S$ level is measured (block 186). A determination is then made as to whether $CAP_S$ is greater than $CAP_{MIN}$ (block 188). If not (NO branch of block 188), then S is again incremented and a new $CAP_S$ is measured (block 186) and the determination is again made (block 188). If so (YES branch of block 188), then the threshold of hearing (T) is set as being equal to the most recent value of S (i.e., that value of stimulus S which produces a $CAP_S$ greater than $CAP_{MIN}$) less a prescribed small value, $k_T$ (block 190).

Once T has been determined (at block 190), the stimulus value S is again incremented (block 192) by a prescribed increment, and a corresponding measure of the MER is made, $MER_S$ (block 192). A determination is then made as to whether $MER_S$ is greater than $MER_{MIN}$ (block 194). If not (NO branch of block 194), then a determination is made as to whether any form of behavioral distress is noted (block 196). If so, the fitting session is stopped and the results evaluated (block 199). If not (NO branch of block 196), then S is again incremented and a corresponding value of $MER_S$ is again measured (block 192), and a new determination is made as to whether $MER_S$ is greater than $MER_{MIN}$ (block 194). If $MER_S$ is greater than $MER_{MIN}$, then the setting for the MCL is determined as the most recent value of S plus a prescribed small value, $k_M$ (block 198).

Thus, as seen in FIG. 4, a method of fitting is presented wherein the dynamic range of electrical stimulation desirable to be applied by an ICS is determined by: (1) determining the low end of the dynamic range by searching for and finding $CAP_S$, the electrical stimulation that produces a compound action potential as sensed electronically from the cochlea, and (2) determining the high end of the dynamic range by searching for and finding $MER_S$, the intensity of the electrical stimulation that produces a middle ear reflex.

Figure 5:
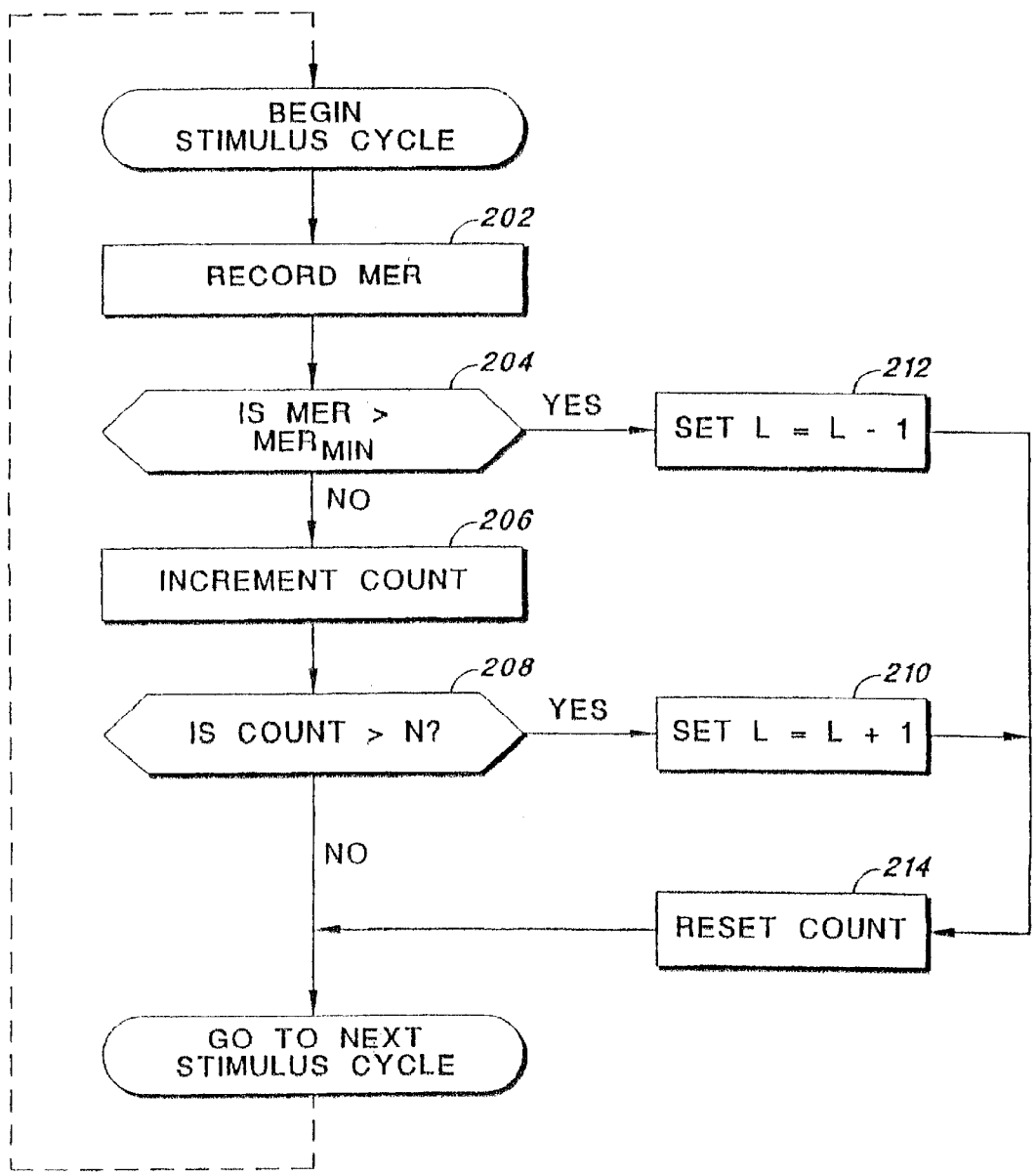
FIG. 5 is a flow chart that shows one technique for automatically adjusting the loudness after every stimulus cycle during use of the ICS.

Turning next to FIG. 5, a simplified flow chart is presented that shows one technique for automatically adjusting the loudness after every stimulus cycle during use of the ICS. Such method or technique may be used with the implant 50 shown in FIG. 1 when coupled to an appropriate speech processor, or μC 52. In carrying out the method shown in FIG. 5, it is assumed that the stimulus level may be increased or decreased in programmable increments, and that the current stimulus level is L. Thus, if L is set to be equal to L=L-1, then that means the stimulus level is decreased by a prescribed increment; and if L is set to be equal to L=L+1, then that means the stimulus level is increased by a prescribed increment. At the beginning of each stimulation cycle, a first step involves measuring the MER (block 202) corresponding to the current stimulus level L by monitoring the signal sensed at the stapedius or tensor tympani electrode 54. A determination is then made as to whether the monitored MER is greater than $MER_{MIN}$ (block 204). If so (YES branch of block 204), then that means the stimulus level should be decreased slightly from its current value, so the next stimulus is set to a value that is one increment lower (L-1) than the current value (block 212). If, on the other hand, the monitored MER is less than $MER_{MIN}$ (NO branch of block 204), then that means there is still some room to increase the stimulus level above its current value. Such increase is made over a prescribed number of stimulation cycles under control of a cycle counter which can reach a maximum value N. For each stimulation cycle during which no adjustment is made to the stimulus level, the count is incremented (block 206), and a determination is then made (after incrementing the count) as to whether the stimulus count has reached its maximum value (block 208). In this way, so long as the stimulus level produces an MER less than $MER_{MIN}$, it takes N passes, or N stimulation cycles, before an adjustment to the stimuluous level is made. The parameter N thus serves as a programmable means for adjusting how quickly or rapidly the stimulous value is increased. Once the value of N is reached (YES branch of block 208), then the stimulous value is increased one increment to L+1 (block 210), and the cycle counter is reset (block 214). Similarly, the cycle counter is reset whenever the stimulous level is decreased one increment (block 212). Thus, each time an adjustment is made to the stimuluous level, the cycle counter is reset, and the process repeats.

It is thus seen that by using the automatic adjustment process shown in FIG. 5, the presence or absence of the middle ear reflex is used to automatically and continuously adjust the intensity of the electrical stimulation provided to the patient, thereby providing a type of automatic gain control (AGC) based on middle ear reflexes. The patient is thus relieved of the slow and tedious process of making frequent manual adjustments of the loudness control on the speech processor.

While the invention herein disclosed has been described by means of specific embodiments and applications thereof, numerous modifications and variations could be made thereto by those skilled in the art without departing from the scope of the invention set forth in the claims.

What is claimed is:

1. A self-adjusting implantable cochlear stimulator (ICS) system comprising cochlea stimulus means for selectively generating a stimulus of a specified intensity on any one of a plurality of channels and evoked potential sensing means for sensing an evoked potential in response to a stimulus generated by the stimulus means, comprising:

middle ear reflex sensing means for sensing a middle ear reflex in response to a stimulus applied by the stimulus means; and microcontroller means for controlling the cochlea stimulus means, evoked potential sensing means and middle ear reflex sensing means to determine the stimulation threshold and most comfortable loudness of the ICS.

2. The self-adjusting ICS of claim 1 wherein said microcontroller means includes:

first means coupled to the middle ear reflex sensing means for determining whether a middle ear reflex (MER) occurs in response to a stimulus of a prescribed intensity being applied to a selected channel by the stimulus means;

second means for increasing the intensity of the stimulus in prescribed increments until a MER occurs, the value of the stimulus that produces a MER comprising a first stimulation threshold; and third means for administering an evoked potential test using stimuli having a starting intensity value derived from the first stimulation threshold in order to zero-in on a second stimulation threshold, the second stimulation threshold representing a most comfortable loudness (MCL) threshold.

3. The self-adjusting apparatus of claim 2 wherein said first means includes an implanted stapedius reflex electrode connected to implanted processing circuitry.

4. The self-adjusting apparatus of claim 2 wherein the implanted processing circuitry includes an amplifier, a bandpass filter and an analog-to-digital converter, wherein a signal sensed through the implanted stapedius reflex electrode is amplified, filtered and converted to a digital signal.

5. The self-adjusting apparatus of claim 2 wherein said third means includes an implanted cochlear electrode array connected to a blanking amplifier, said blanking amplifier including means for shutting down coincident with the delivery of a stimulus by said ICS to prevent any stimulus-created artifacts from being sensed through the blanking amplifier.

6. A method for self-adjusting the stimulus parameters of an implantable cochlear stimulator (ICS) by determining a dynamic range of electrical stimulation to be applied by the ICS to a patient, said ICS including means for applying an electrical stimulus to the cochlea of the patient, the method being characterized by:

determining a low end of the dynamic range by measuring the intensity of electrical stimulation that produces a compound action potential (CAP) sensed electronically by sensing means coupled with the cochlea, and determining a high end of the dynamic range by measuring the intensity of electrical stimulation that produces a middle ear reflex (MER) sensed electronically by MER sensing means.

7. The method of claim 6 further including determining the MER by sensing electromyographic signals from at least one middle ear muscle.

8. The method of claim 7 wherein sensing electromyographic signals comprises sensing electromyographic signals through wire electrodes affixed in or near at least one middle ear muscle.

9. The method of claim 7 wherein the at least one middle ear muscle comprises the stapedius muscle.

10. The method of claim 7 wherein the at least one middle ear muscle comprises the tensor tympani.

11. The method of claim 7 wherein determining the MER comprises using electronic means for extracting an electronic signal having a single value indicative of the amplitude of the electromyographic potential.

12. The method of claim 6 further comprising determining the MER by measuring acoustic impedance.

13. The method of claim 6 wherein measuring the intensity of electrical stimulation that produces an MER comprises:

(a) measuring the stapedius reflex of the patient;

(b) using the stapedius reflex measured in step (a) as a rough estimate of a most comfortable level (MCL) of stimulus;

(c) setting the intensity of an initial stimulus to the rough estimate of the MCL determined in step (b);

(d) applying the initial stimulus to the cochlea;

(e) detecting whether the stimulus applied in step (d) evokes an observable electrical response from the patient;

(f) increasing the intensity of a next stimulus to be applied to the patient by a prescribed amount $\Delta$ if no evoked response is detected in step (e);

(g) decreasing the intensity of a next stimulus to be applied to the patient by a prescribed amount $\Delta$ if an evoked response is detected in step (e);

(h) applying the next stimulus and repeating steps (e)–(g) for a prescribed number of passes, with each pass through steps (e)–(g) using a smaller value for the amount $\Delta$, thereby zeroing-in on the stimulation threshold.

14. The method of claim 13 wherein step (a) comprises measuring the stapedius reflex using an implanted stapedius electrode.

15. The method of claim 13 wherein step (e) comprises detecting whether the stimulus applied to the cochlea evokes an observable electrical response from a cochlear electrode (59) implanted within the patient.

16. A self-adjusting implantable cochlear stimulator (ICS) system comprising:

an implantable cochlear stimulator (ICS);

a plurality of electrodes connected to the ICS through which a stimulus of a specified intensity is selectively applied;

a first sensing electrode connected to a first amplifier and first filter that senses an evoked potential in response to a stimulus generated by the ICS;

a second sensing electrode coupled to the middle ear and connected to a second amplifier and a second filter that senses a middle ear reflex in response to a stimulus applied by the ICS; and a microcontroller connected to control the ICS and to receive electrical signals from the first sensing electrode, first amplifier and first filter, and second sensing electrode, second amplifier, and second filter that determines, based on the signals received through the first and second sensing electrodes, a stimulation threshold and most comfortable loudness for the ICS.

17. The self-adjusting ICS system of claim 16 wherein said microcontroller includes:

first processing means responsive to the signals received through the second sensing electrode for determining whether a middle ear reflex (MER) occurs in response to a stimulus of a prescribed intensity being applied to a selected pair of the plurality of electrodes;

second processing means for increasing the intensity of the stimulus in prescribed increments until a MER occurs, the value of the stimulus that produces a MER comprising a first stimulation threshold; and third processing means for administering an evoked potential test using stimuli having a starting intensity value derived from the first stimulation threshold in order to zero-in on a second stimulation threshold, the second stimulation threshold representing a most comfortable loudness (MCL) threshold.

18. The self-adjusting ICS system of claim 16 wherein said second sensing electrode comprises a stapedius reflex electrode.

19. The self-adjusting ICS system of claim 16 wherein said second sensing electrode comprises a tensor tympani electrode.

20. The self-adjusting ICS system of claim 16 wherein said first and second filters comprise bandpass filters.

* * * * *